(12) United States Patent
Bauss

(10) Patent No.: US 10,733,909 B2
(45) Date of Patent: *Aug. 4, 2020

(54) MEDICAMENT INJECTION DEVICE OR INJECTION MOCK-UP DEMO DEVICE WITH MOTION DETECTOR TO LOG AND TRACK USER BEHAVIOUR

(71) Applicant: SHL MEDICAL AG, Zug (CH)

(72) Inventor: Markus Bauss, Lengdorf (SE)

(73) Assignee: SHL MEDICAL AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/740,218

(22) Filed: Jan. 10, 2020

(65) Prior Publication Data

US 2020/0152087 A1 May 14, 2020

Related U.S. Application Data

(63) Continuation of application No. 15/504,971, filed as application No. PCT/EP2015/067799 on Aug. 3, 2015, now Pat. No. 10,593,232.

(30) Foreign Application Priority Data

Aug. 19, 2014 (SE) ........................................ 1450959

(51) Int. Cl.
*G09B 23/28* (2006.01)
*A61M 5/24* (2006.01)
(Continued)

(52) U.S. Cl.
CPC ....... *G09B 23/285* (2013.01); *A61M 5/14244* (2013.01); *A61M 5/20* (2013.01); *A61M 5/24* (2013.01); *A61M 5/3202* (2013.01); *G09B 19/00* (2013.01); *A61M 2205/18* (2013.01); *A61M 2205/332* (2013.01); *A61M 2205/3317* (2013.01); *A61M 2205/3553* (2013.01); *A61M 2205/3561* (2013.01); *A61M 2205/3576* (2013.01); *A61M 2205/3584* (2013.01);
(Continued)

(58) Field of Classification Search
None
See application file for complete search history.

(56) References Cited

U.S. PATENT DOCUMENTS

2010/0280329 A1\* 11/2010 Randlov et al. ... A61B 5/14532
600/300
2011/0049060 A1\* 3/2011 Uy .......................... C02F 1/008
210/749

(Continued)

*Primary Examiner* — Jason T Yen
(74) *Attorney, Agent, or Firm* — McDonnell Boehnen Hulbert & Berghoff LLP

(57) ABSTRACT

The present disclosure relates to a mock-up medicament injector for training purposes or an actual medicament injection device (1) comprising a sensor device (2) configured to detect movements of the whole device, and a logging device (3) configured to record said movements and thus track user behaviour of the device. The sensor can be e.g. an accelerometer, gyroscope or magnetometer. The device can communicate the logged data either in real time or at a later point in time from its memory to an external computer device. The present disclosure also relates to a corresponding method for tracking behaviour of a user using the medicament injector or training device (1).

18 Claims, 2 Drawing Sheets

(51) Int. Cl.
     *A61M 5/20*      (2006.01)
     *A61M 5/142*     (2006.01)
     *G09B 19/00*     (2006.01)
     *A61M 5/32*      (2006.01)
     *G16H 10/60*         (2018.01)
     *G16H 15/00*         (2018.01)

(52) U.S. Cl.
     CPC ..... *A61M 2205/50* (2013.01); *A61M 2205/52* (2013.01); *A61M 2205/8206* (2013.01); *A61M 2230/63* (2013.01); *G16H 10/60* (2018.01); *G16H 15/00* (2018.01)

(56) References Cited

U.S. PATENT DOCUMENTS

| | | | |
|---|---|---|---|
| 2011/0313349 A1* | 12/2011 | Krulevitch | A61M 5/3129 604/65 |
| 2012/0330571 A1* | 12/2012 | LaCourse | G09B 23/285 702/41 |
| 2013/0029605 A1* | 1/2013 | Patil | H04R 1/1091 455/41.3 |
| 2013/0236872 A1* | 9/2013 | Laurusonis | G09B 23/285 434/262 |
| 2014/0324463 A1* | 10/2014 | Buck | G16H 10/60 705/3 |

\* cited by examiner

MEDICAMENT INJECTION DEVICE OR INJECTION MOCK-UP DEMO DEVICE WITH MOTION DETECTOR TO LOG AND TRACK USER BEHAVIOUR

TECHNICAL FIELD

The invention relates to a device, a system and a method for medicament delivery.

BACKGROUND

US patent application with publication no US 2013/0236872 describes reusable automatic injection training devices, and components thereof, to simulate and/or mimic an operation of an actual automatic injection device.

UK patent application no GB 2490723 describes a syringe for use in a human factors study.

U.S. Pat. No. 8,556,865 describes a module configured to be attached to a disposable drug delivery pen or a reusable drug delivery pen so that the module may: determine dosage selected, inject the selected dosage, duration of injection, time of injection, whether the pen has been primed or shaken to thoroughly mix up insulin mixtures, transmit information relating to insulin dosage and injection to a data management unit, provide reminders, error warning or message on improper usage or reusage of needles, track amount of drug remaining on board the pen or during usage of pen with respect to expiry of the drug on board, or provide an audible alarm for locating a misplaced pen and module.

SUMMARY

An object of embodiments of the present invention is to facilitate medicament delivery.

It is a further object of embodiments of the present invention to facilitate analysis of how users handle the devices and thereby provide improved training for the correct use of medicament delivery devices.

According to a first aspect, it is presented a medicament delivery device comprising a sensor device and a logging device. The sensor device is configured to detect a motion of the medicament delivery device. The logging device is configured to track user behaviour of the medicament delivery device, which user behaviour is based on a motion detected by the sensor device. By tracking the motion of the medicament delivery device, tracking of user behaviour for study, training or compliance is improved, which facilitates medicament delivery.

The sensor device generally refers to any kind of sensor capable of detecting movement. Preferably, the sensor device may comprise one or more of the following sensors: a magnetometer, a gyroscope, and/or an accelerometer, wherein high precision tracking of motion is improved.

The medicament delivery device may further comprise a memory device configured to store data from the logging device, wherein tracking is facilitated for a user thereof. The memory device may comprise a non-volatile memory.

The medicament delivery device may further comprise a communication device configured to transmit data from the logging device to a computer device external of the medicament delivery device.

According to one embodiment, the communication device may be configured to wirelessly or wired transmit real time data from the logging device, wherein real time visualization of the tracking is achieved.

According to another embodiment, the communication device is configured to wirelessly or wired transmit stored data in the memory device.

The logging device may be configured to start tracking user behaviour when the medicament delivery device is removed from a transportation box, whereby tracking is facilitated for a user thereof.

According to a further embodiment, the logging device may be configured to start tracking user behaviour when a protective cap of the medicament delivery device is removed, whereby tracking is facilitated for a user thereof.

The medicament delivery device may be an actual delivery device for injection of a medicament, or may be a mock-up demo device for human factors study or for training.

According to a second aspect, it is provided a method for user behaviour tracking of a medicament delivery device. The method comprises the steps of: detecting a motion of the medicament delivery device; and tracking a user behaviour of the medicament delivery device based on the detected motion.

According to a third aspect, it is provided a medicament delivery system. The medicament delivery system comprises a medicament delivery device, a computer device external of the medicament delivery device having a display device. The medicament delivery device comprises a sensor device, a logging device, and a communication device. The sensor device is configured to detect a motion of the medicament delivery device. The logging device is configured to track user behaviour of the medicament delivery device, which user behaviour is based on a motion detected by the sensor device. The communication device is configured to transmit wirelessly and/or wired real time data from the logging device to the computer device external of the medicament delivery device or to a remote location for later analysis. The communication device may also be configured to transmit wirelessly and/or wired data stored in a memory device from the logging device to the computer device external of the medicament delivery device or to a remote location for later analysis.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

Figure 1:
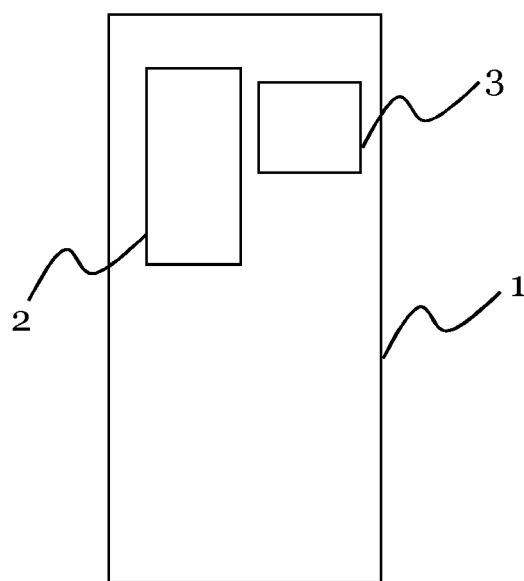
FIG. 1 is a schematic diagram illustrating a medicament delivery device for an embodiment presented herein.

The invention will now be described more fully with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

There is today an interest in being able to capture additional information of how end users use specific medicament delivery devices. On one hand, this is important information, when it comes to the development of new medicament delivery devices, e.g. high volume injections. On the other hand, the technology can fulfil current market needs, as starting a completely new generation of connected training devices as well as supporting better compliance and adherence.

Smart sensors, including temperature, motion logging and other ways of tracking physical parameters are today available. In this context, especially by implementation of the new BLE (Bluetooth Low Energy)/Bluetooth Smart technology, data logging systems may be developed, that survive for a very long time period, with a coin size battery.

The design of a medicament delivery device impacts the functionality and behaviour of a user performing an injection. It is desirable to know how a modification of a design of a medicament delivery device has direct impact on the user's behaviour and on the performance of the medicament delivery device.

To visualize and to capture such data may be advantageous for a deeper evaluation of the behaviour of the customers in combination with a specific product.

A real time, high precision logging system may be provided by use of a sensor device which comprises one or more of the following sensors: a gyroscope, an accelerometer and/or a magnetometer. Using the sensor device for real time visualization, software may be provided, that shows real time visualization on a computer device external of the medicament delivery. The computer device external of the medicament delivery device comprises a display device. Examples of such computer device may be such as a lap-top, a smart mobile device, a tablet or similar.

Further, a communication device is also provided and configured to transmit data from the logging device to the computer device external of the medicament delivery device. The transmissions of the real time data may be performed wirelessly and/or wired. It can also be desirable to transmit to a remote location. The communication device shall be configured to perform such a transmission using known technologies to transmit to remote locations.

Sometime it could be desirable to store the data for later analysis. Thus, a memory device may be provided where data received from the logging system may be stored and from which that stored data may be retrieved at a later stage for analysis. The memory device may be a non-volatile memory.

The system would not only allow motion tracking, but by the smart sensors also allow recording information about the activation status of the medicament delivery device, or even further information, This could happen, e.g. by sensing the electromagnetic field of an auto injector spring. The electromagnetic field is for instance different for a spring that has been deployed vs. a non-deployed spring.

By direct feedback, a system of an app, such as a smartphone application or to software, and a medicament delivery device may become a tool providing immediate feedback to analyse a user's handling behaviour.

FIG. 1 is a schematic diagram illustrating a medicament delivery device for an embodiment presented herein.

The medicament delivery device 1 comprises:
a sensor device 2 configured to detect a motion of the medicament delivery device 1; and
a logging device 3 configured to track user behaviour of the medicament delivery device 1, which user behaviour is based on a motion detected by the sensor device 2.

By motion of the medicament delivery device 1, movement of the whole device is meant.

The sensor device 2 may comprise one or more of the following sensors: a magnetometer, a gyroscope, and/or an accelerometer. A magnetometer may by used to detect the position of an auto injector needle of the medicament delivery device 1. A gyroscope may be used to detect the position of the medicament delivery device 1. An accelerometer may be used to detect movement in a direction. By use of a combination of a gyroscope and three accelerometers, a high precision tracking may be provided.

The medicament delivery device 1 may further comprise a memory device such as a non-volatile memory to store data from the sensor device 2 and/or from the logging device 3. The non-volatile memory may e.g. be a read-only memory, flash memory, ferroelectric RAM (F-RAM), most types of magnetic computer storage devices (e.g. hard disks, floppy disks, and magnetic tape), optical discs. The non-volatile memory may be removable, to be inserted into a reader of an external device. The medicament delivery device 1 may further be provided with a contact interface, allowing stored data to be uploaded to an external device through a cable connection. Further, the medicament delivery device 1 may be provided with a communication device allowing real data and/or stored data to be uploaded to the external device. The communication device is configured to wirelessly and/or wired transmit real time data from the logging device or to transmit stored data from the memory device. The communication device may be provided with e.g. wi-fi, Bluetooth or BLE.

The logging device 3 may be configured to start tracking user behaviour when the medicament delivery device 1 is removed from a transportation box or when a protective cap is removed from the medicament delivery device. The user behaviour data will be stored in the memory device e.g. in a non-volatile memory in the medicament delivery device. A user will in this case not need to remember to start any initiations, or try to figure out how to connect the medicament delivery device to an external device, wired or wirelessly. I.e. the user does not have to do anything different than he does with a conventional device. The device may automatically log, e.g. within a time period of more than a week from taking the product out of the box, the use of the device and behaviour of the user. To start tracking when the device is removed from the transportation box or when the protective cap is removed from the medicament delivery device, a disconnected battery may be included in the device. When the device is removed from the box or when the protective cap is removed from the medicament delivery device, an insulation sheet may be removed from between the battery and a contact pad.

The medicament delivery device 1 may be an actual delivery device 1 for delivery of a medicament. By tracking the user behaviour, it is possible to later identify if a user have been using the medicament delivery device 1 in a correct manner or not. By transmitting real time data to an external device, visualization of direct feedback may be provided.

The medicament delivery device may be a mock-up demo device for human factors study or for training.

The medicament delivery device may be provided with both a data storage as well as a real time data transmitter. By being directly connected via e.g. Bluetooth to a tablet computer to sense real time data, human factor/patient study in real time can be made to see what a patient does with the device/how he handles it. With a data storage, the same data may be provided for further evaluation in the future, by comparison to future data.

For human factors study, a multi-device may be provided, that would allow tracking patients' behaviour with different devices or devices that have been equipped with modified parts (e.g. different activation button, different surface of device etc,).

For training, a patient may use a medicament delivery training device at home. Once he returns the device to a study organizer, the organizer will be able to evaluate the data, e.g. together with the patient, to understand, if the patient had any issues and if he complied with the handling instructions.

Figure 2:
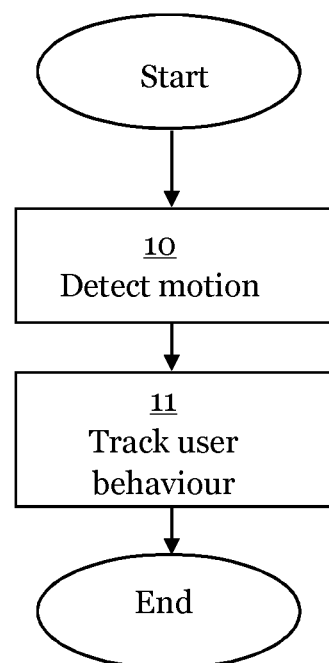
FIG. 2 is a flow chart illustrating a method for an embodiment presented herein.

FIG. 2 is a flow chart illustrating a method for an embodiment presented herein.

The method for user behaviour tracking of a medicament delivery device 1, comprises the steps of:
  detecting 10 a motion of the medicament delivery device 2; and
  tracking 11 a user behaviour of the medicament delivery device 1 based on the detected motion.

Figure 3:
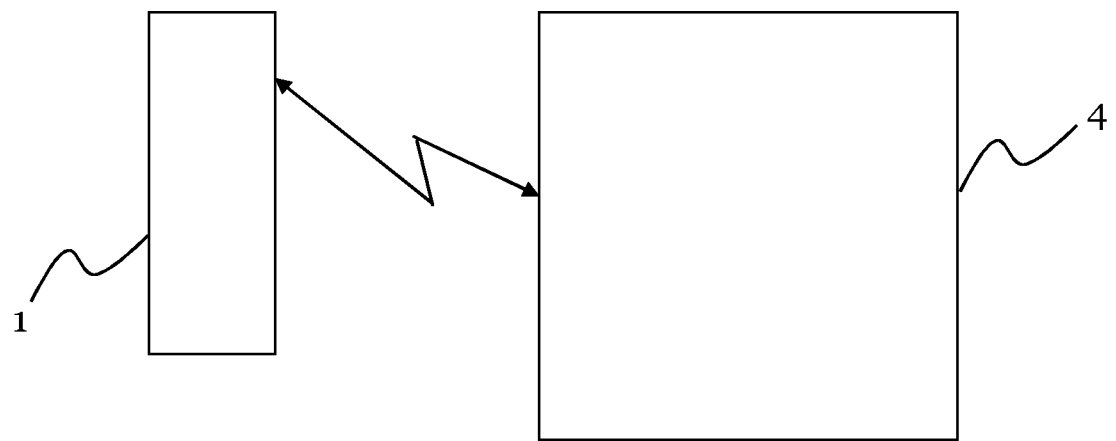
FIG. 3 is a schematic diagram illustrating a medicament delivery system for an embodiment presented herein.

FIG. 3 is a schematic diagram illustrating a medicament delivery system for an embodiment presented herein.

The medicament delivery system comprises:
  a medicament delivery device 1, a computer device external of the medicament delivery device 1 having a display device 4,
  the medicament delivery device comprises:
    a sensor device 2 configured to detect a motion of the medicament delivery device 1;
    a logging device 3 configured to track user behaviour of the medicament delivery device 1, which user behaviour is based on a motion detected by the sensor device 2; and
    communication device configured to transmit wirelessly or wired real time data from the logging device or data stored in a memory device from the logging device to the display device 4.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A medicament delivery device comprising:
  a cap that is removably attached to a distal portion of the medicament delivery device;
  a battery;
  a contact pad;
  an insulating sheet positioned between the battery and the contact pad;
  a sensor configured to detect information about the medicament delivery device; and
  a communication device configured to transmit real time data to an external device, where the real time data comprises the information detected by the sensor,
  wherein the insulating sheet is removed from between the battery and the contact pad when the cap and the distal portion are moved relative to each other or when the medicament delivery device is removed from a transportation box.

2. The medicament delivery device of claim 1 wherein the external device comprises a computer.

3. The medicament delivery device of claim 1 wherein the contact between the battery and the contact pad starts tracking of the real time data.

4. The medicament delivery device of claim 1, wherein the medicament delivery device comprises a gyroscope.

5. The medicament delivery device of claim 1, wherein the medicament delivery device comprises an accelerometer.

6. The medicament delivery device of claim 1, wherein the medicament delivery device is configured for injection of a medicament.

7. The medicament delivery device of claim 1, wherein the medicament delivery device is a mock-up demo device configured for human factors study.

8. The medicament delivery device of claim 1, wherein the medicament delivery device further comprises a logging device configured to start tracking motion of the medicament delivery device when the medicament delivery device is removed from the transportation box or the cap is removed.

9. The medicament delivery device of claim 1, wherein the medicament delivery device is configured for training.

10. The medicament delivery device of claim 1, further comprising a memory device configured to store the real time data.

11. The medicament delivery device of claim 10, where the communication device is configured to transmit the real time data from the memory device to the external device.

12. The medicament delivery device of claim 11, wherein the communication device is configured to transmit, via a wired connection, data from the memory device.

13. The medicament delivery device of claim 11, wherein the communication device is configured to wirelessly transmit data from the memory device.

14. The medicament delivery device of claim 1, wherein the communication device is configured to wirelessly transmit the real time data to the external device.

15. The medicament delivery device of claim 1, wherein the communication device is configured to transmit, via a wired connection, the real time data to the external device.

16. A method of transmitting real time data containing information relating to a medicament delivery device, where the medicament delivery device has a protective cap attached to a distal portion of the medicament delivery device, the method comprising:
  (a) moving the protective cap relative to the distal portion of the medicament delivery device, thereby causing removal of an insulating sheet from between a battery and a contact pad of the medicament delivery device; or
  (b) removing the medicament delivery device from a box, thereby causing removal of the insulating sheet from between the battery and the contact pad,
  detecting, via a sensor, the information about the medicament delivery device; and
  transmitting to an external device the real time data comprising the information.

17. The method of transmitting real time data according to claim 16, wherein removal of the insulating sheet starts the transmission of the real time data.

18. A medicament delivery system comprising:
  a medicament delivery device and a computing device that is external to the medicament delivery device,
  wherein the medicament delivery device comprises:

a cap removably attached to a distal portion of the medicament delivery device;

a battery;

a contact pad;

an insulating sheet positioned between the battery and the contact pad;

a sensor configured to detect information about the medicament delivery device; and a communication device configured to transmit real time data to the computing device, where the real time data comprises the information detected by the sensor, wherein the insulating sheet is removed from between the battery and the contact pad when the cap and the distal end are moved relative to each other or when the medicament delivery device is removed from a transportation box.

* * * * *